(12) United States Patent
Bouvier et al.

(10) Patent No.: US 11,358,118 B2
(45) Date of Patent: Jun. 14, 2022

(54) ZEOLITE ADSORBENTS CONTAINING STRONTIUM

(71) Applicants: Arkema France, Colombes (FR); IFP Energies Nouvelles, Rueil-Malmaison (FR)

(72) Inventors: Ludivine Bouvier, Orthez (FR); Javier Perez-Pellitero, Lyons (FR); Marie-Laurence Labede, Lescar (FR); Guillaume Blancke, Francheville (FR)

(73) Assignees: Arkema France, Colombes (FR); IFP Energies Nouvelles, Rueil-Malmaison (FR)

( * ) Notice: Subject to any disclaimer, the term of this patent is extended or adjusted under 35 U.S.C. 154(b) by 33 days.

(21) Appl. No.: 16/955,400

(22) PCT Filed: Dec. 17, 2018

(86) PCT No.: PCT/FR2018/053327
§ 371 (c)(1),
(2) Date: Jun. 18, 2020

(87) PCT Pub. No.: WO2019/122649
PCT Pub. Date: Jun. 27, 2019

(65) Prior Publication Data
US 2021/0069671 A1    Mar. 11, 2021

(30) Foreign Application Priority Data
Dec. 22, 2017 (FR) .................................. 1763036

(51) Int. Cl.
| B01J 20/18 | (2006.01) |
| C01B 39/22 | (2006.01) |
| C07C 7/13 | (2006.01) |
| B01J 29/08 | (2006.01) |
| B01J 37/30 | (2006.01) |
| B01J 20/30 | (2006.01) |
| B01J 20/28 | (2006.01) |

(52) U.S. Cl.
CPC .......... B01J 20/18 (2013.01); B01J 20/2803 (2013.01); B01J 20/3071 (2013.01); B01J 20/3078 (2013.01); B01J 20/3085 (2013.01); B01J 29/08 (2013.01); B01J 37/30 (2013.01); C01B 39/22 (2013.01); C07C 7/13 (2013.01); B01J 2229/186 (2013.01)

(58) Field of Classification Search
CPC ...... B01J 29/08; B01J 2229/186; B01J 37/30; B01J 20/2803; B01J 20/3071; B01J 20/3078; B01J 20/18; B01J 20/3085; C01B 39/22; C07C 7/13; C07C 15/08
USPC ......... 502/60, 79, 85, 64, 69, 400, 407, 411; 423/700; 585/820, 828
See application file for complete search history.

(56) References Cited

U.S. PATENT DOCUMENTS

| 2,985,589 | A | 5/1961 | Broughton et al. |
| 3,558,730 | A | 1/1971 | Neuzil |
| 3,558,732 | A | 1/1971 | Neuzil |
| 3,626,020 | A | 12/1971 | Neuzil |
| 3,663,638 | A | 5/1972 | Neuzil |
| 3,960,774 | A | 6/1976 | Rosback |
| 3,997,620 | A | 12/1976 | Neuzil |
| 4,255,607 | A | 3/1981 | Miyake et al. |
| 4,402,832 | A | 9/1983 | Gerhold |
| 4,498,991 | A | 2/1985 | Oroskar |
| 4,957,514 | A | 9/1990 | Golden et al. |
| 5,177,299 | A | 1/1993 | McCulloch et al. |
| 5,284,992 | A | 2/1994 | Hotier et al. |
| 5,629,467 | A | 5/1997 | Hotier et al. |
| 5,916,836 | A * | 6/1999 | Toufar .................. C01B 39/026 502/86 |
| 6,143,057 | A * | 11/2000 | Bulow ................... B01D 53/02 502/79 |
| 6,884,918 | B1 | 4/2005 | Plee et al. |
| 7,785,563 | B2 | 8/2010 | Ryoo et al. |
| 10,675,607 | B2 | 6/2020 | Laroche et al. |
| 2011/0105301 | A1 | 5/2011 | Wang |
| 2015/0306565 | A1 | 10/2015 | Bouvier et al. |
| 2018/0201555 | A1 | 7/2018 | LaRoche et al. |

FOREIGN PATENT DOCUMENTS

| FR | 2329623 A1 | 5/1977 |
| FR | 2681066 A1 | 3/1993 |
| FR | 2789914 A1 | 8/2000 |
| WO | 2013106816 A1 | 7/2013 |
| WO | 2014090771 A1 | 6/2014 |
| WO | 2017005907 A1 | 1/2017 |

OTHER PUBLICATIONS

Breck, D., "Zeolites Molecular Sieves", John Wiley & Sons, 1973, 4 pages.
Inayat et al., "Assemblies of Mesoporous FAU-Type Zeolite Nanosheets", Angew. Chem. Int. Ed., 2012, vol. 51, pp. 1962-1965.
International Search Report and Written Opinion for International Application PCT/FR2018/053327, dated Mar. 20, 2019, 9 pages.
International Search Report and Written Opinion for International Application PCT/FR2018/053328, dated Feb. 12, 2019, 9 pages.
Ruthven et al., "Principles of Adsorption and Adsorption Processes", John Wiley & Sons, 1984, 453 pages.
Verboekend et al., "Hierarchical Y and USY Zeolites Designed by Post-Synthetic Strategies", Adv. Funct. Mater., 22, (2012), pp. 916-928.
Mazzotti, M., et al., "Robust Design of Countercurrent Adsorption Separation Process: 2. Multicomponent Systems," Nov. 1994, pp. 1825-1842, vol. 40(11), AIChE Journal.
Indian Examination Report for Indian Application No. 202017024115, dated Dec. 24, 2021, with translation, 6 pages.
Indian Examination Report for Indian Application No. 202017025692, dated Jan. 6, 2022, with translation, 5 pages.

* cited by examiner

*Primary Examiner* — Elizabeth D Wood
(74) *Attorney, Agent, or Firm* — RatnerPrestia

(57) ABSTRACT

The present invention relates to zeolite adsorbents based on agglomerated crystals of zeolite(s) comprising barium and strontium These adsorbents have applications in the separation of fractions of aromatic C8 isomers and in particular xylene.

9 Claims, No Drawings

ZEOLITE ADSORBENTS CONTAINING STRONTIUM

CROSS-REFERENCE TO RELATED APPLICATIONS

This is the national phase of International Application No. PCT/FR2018/053327, filed 17 Dec. 2018, which claims priority to French Application No. 1763036, filed 22 Dec. 2017. The disclosure of each of these applications is incorporated herein by reference in its entirety for all purposes.

The invention relates to adsorbents based on agglomerated crystals of zeolite X comprising barium and strontium.

These adsorbents can be used more particularly for the liquid-phase or gas-based production of very pure para-xylene from a feedstock of aromatic hydrocarbons containing isomers comprising 8 carbon atoms.

The high-purity para-xylene market is considered to be a widely expanding market, its outlets being mainly the production of terephthalic acid (PTA) obtained by oxidation of para-xylene, on which are based the polyester fibres used for clothing and polyethylene terephthalate (PET) resins and films.

High-purity para-xylene is nowadays usually obtained by producing it through exploitation of xylenes according to a process termed "C8 aromatic loop", including steps of separation (elimination of the heavy compounds in the "xylene column", extraction of para-xylene) and isomerization of xylenes. Extraction of high-purity para-xylene by selective adsorption is moreover well known from the prior art.

The technical background describing the production of very high-purity para-xylene is illustrated in patent FR 2 681 066 (Institut Français du Pétrole [French Petroleum Institute]), and is based on the separation of para-xylene from a feedstock of aromatic hydrocarbons essentially comprising 8 carbon atoms within an adsorber by contact with a bed of zeolite adsorbent in the presence of a suitable desorption solvent (desorbent).

It is also known in the prior art that zeolite adsorbents comprising at least Faujasite (FAU) zeolite type X or Y and comprising, in addition to the sodium cations, barium, potassium or strontium ions, alone or as a mixture, are effective for selectively adsorbing para-xylene in a mixture of aromatic hydrocarbons.

U.S. Pat. Nos. 3,558,732 and 4,255,607 show that zeolite adsorbents comprising aluminosilicates based on potassium or based on barium, or else based on potassium and barium, are effective for separating the para-xylene present in aromatic C8 fractions (fractions comprising aromatic hydrocarbons comprising 8 carbon atoms).

U.S. Pat. No. 3,997,620 presents agglomerates in which the agglomeration binder is not zeolitized, said agglomerates being exchanged with barium or with strontium, such that the Ba/Sr weight ratio is between 1:1 and 15:1.

More particularly, this document teaches that adsorbents based on zeolites of type X or type Y comprising barium and strontium, in their exchangeable cationic sites, with a barium/strontium weight ratio of approximately 1:1 to approximately 15:1, can advantageously be used in a process for recovering para-xylene. With this ratio, the advantage observed is an improved para-xylene selectivity with respect to the desorbent, para-diethylbenzene, but also an improved para-xylene selectivity with respect to the other xylene isomers.

Besides this document showing a certain advantage, from the viewpoint of selectivity, for agglomerates containing high proportions of strontium, it nevertheless remains the case that, in the scientific literature, as in the patent literature, the documents teach mainly that zeolites comprising barium cations or barium and potassium cations prove to be particularly effective in terms of selectivity for the separation of isomers of aromatic hydrocarbons comprising 8 carbon atoms. The industrial zeolites used in these isomer separation applications are conventionally prepared from zeolites comprising sodium as compensating cation, then the sodium ions are exchanged with barium ions or barium and potassium ions.

These exchange operations are customarily carried out using an aqueous solution of a barium halide, and in particular of barium chloride ($BaCl_2$). However, since very high-purity barium chloride, as required for the synthesis of said zeolites, is expensive, the exchange with this very pure salt proves to be increasingly less competitive for large-scale zeolite preparations.

This is because barium chloride is usually obtained from ores, such as for example barite or benstonite, and these ores generally comprise other alkali or alkaline-earth metals, including strontium, in particular. Consequently, the various commercially available sources of barium ions, for example in the form of barium chloride, when they are not of very high purity, may contain not insignificant amounts of impurities in the form of strontium salts, for example about 500 ppm by weight to a few percent by weight of strontium chloride The costs of sources of barium in the form of barium chloride of very high purity and also the environmental impact of the operations of purifying barium chloride mean that alternatives must be found which dispense with these problems, while at the same time making it possible to maintain maximum effectiveness, in particular in terms of selectivity and productivity, when the barium-exchanged agglomerates are used for recovering para-xylene in aromatic C8 fractions.

In addition, it is always advantageous to be able to have several suppliers of barium sources, in particular barium chloride, while at the same time being able to dispense with drastic purity conditions, and to have various sources, since some may prove to be less "pure" in terms of barium contents than others which contain variable amounts of strontium chloride.

It has now been discovered that the abovementioned objectives can be achieved, in all or at least in part, by virtue of the present invention which is now set out in the description which follows. Other further objectives may emerge in the detailed description below.

Thus, and according to a first aspect, the present invention relates to an adsorbent based on agglomerated crystals of zeolite(s), said agglomerate comprising:
  at least crystals of FAU zeolite(s), with an Si/Al molar ratio of between 1.00 and 1.50, limits included,
  a weight content of barium ions ($Ba^{2+}$), expressed by weight of barium oxide (BaO), strictly greater than 30%, preferably strictly greater than 33%, more preferably a content of between 34% and 42%, limits included, and entirely preferably of between 34% and 40%, limits included, relative to the total weight of the adsorbent,
  a weight content of strontium ions ($Sr^{2+}$), expressed by weight of strontium oxide (SrO), strictly greater than 0.1% and strictly less than 3%, preferably of between 0.15% and 2.9%, limits included, more preferably of between 0.15% and 2.5% and entirely preferably of between 0.15% and 2.4%, limits included, relative to the total weight of the adsorbent.

In the present invention, it should be understood that the weight contents expressed in weight of oxides are expressed relative to the total weight of the anhydrous adsorbent (weight corrected with respect to loss on ignition).

The adsorbents according to the invention may also comprise a non-zeolite phase, that is to say a non-crystalline phase which is essentially inert with respect to the adsorption, as explained below. In the case where the adsorbent according to the invention comprises such a non-zeolite phase, the oxide contents defined above take into account oxides included in said non-zeolite phase.

The adsorbent according to the present invention is an adsorbent based on crystals of FAU zeolite of type X. The term "FAU zeolite of type X" is intended to mean zeolites of which the Si/Al atomic ratio is between 1.00 and 1.50, limits included, preferably between 1.00 and 1.45, more preferably between 1.05 and 1.45, limits included, and even more preferably between 1.10 and 1.45, limits included.

Among the zeolites X, it is now commonly accepted to recognize two subgroups known as LSX zeolites and MSX zeolites. The LSX zeolites have an Si/Al atomic ratio equal to approximately 1 and the MSX zeolites have an Si/Al atomic ratio of between approximately 1.05 and approximately 1.15, limits included.

The definition of FAU zeolite also comprises the hierarchically porous FAU zeolites of type X defined above, that is to say hierarchically porous zeolites of type X (HPX zeolite), hierarchically porous zeolites of type MSX (or HPMSX) and hierarchically porous zeolites of type LSX (or HPLSX), and more particularly hierarchically porous FAU zeolites with an Si/Al atomic ratio of between 1.00 and 1.50, limits included, preferably between 1.05 and 1.50, more preferably between 1.05 and 1.40, limits included, and even more preferably between 1.15 and 1.40, limits included.

The term "hierarchically porous zeolite" is intended to mean a zeolite which has both micropores and mesopores, in other words a zeolite which is both microporous and mesoporous. The term "mesoporous zeolite" is intended to mean a zeolite of which the microporous zeolite crystals have, together with the microporosity, internal cavities of nanometric size (mesoporosity), easily identifiable by observation using a transmission electron microscope (TEM), as described for example in U.S. Pat. No. 7,785,563: the observation by transmission electron microscopy (TEM) makes it possible to verify whether the zeolite crystals are solid zeolite crystals (i.e. non-mesoporous) or solid zeolite crystal aggregates or mesoporous crystals or mesoporous crystal aggregates.

The adsorbent according to the invention also encompasses the adsorbents comprising mixtures of two or more FAU zeolites as have just been defined, but also comprising mixtures of one or more FAU zeolites with one or more other zeolites well known to those skilled in the art. However, adsorbents based on crystals of FAU zeolite of type X, as defined above, are preferred.

The structure of the crystals of zeolite(s) in the adsorbent of the present invention can be easily identified by any method known to those skilled in the art and in particular by X-ray diffraction (also known as "XRD analysis").

According to one preferred embodiment, the zeolite adsorbent has an Si/Al atomic ratio of between 1.00 and 2.00, preferably between 1.00 and 1.80, limits included, more preferably between 1.15 and 1.80, limits included, and even more preferably between 1.15 and 1.60, limits included.

In the present document, the term "number-average diameter" or else "size" is used for the crystals of zeolite(s) and for the adsorbent according to the invention. The method of measurement of these parameters is explained below in the description. According to one preferred embodiment of the invention, the number-average diameter of the crystals of zeolite(s) is less than or equal to 1.5 µm, preferably between 0.1 µm and 1.2 µm, more preferably between 0.1 µm and 1.0 µm, limits included.

According to one preferred embodiment, the total weight content of alkali or alkaline-earth metal ions other than $Ba^{2+}$ and $Sr^{2+}$, expressed by weight of alkali or alkaline-earth metal oxides respectively, is less than 5% and is preferably between 0% and 2% and advantageously between 0% and 1%, limits included, relative to the total weight of the adsorbent.

In the context of the present invention, the adsorbents comprising a weight content of sodium ions ($Na^+$), expressed by weight of sodium oxide ($Na_2O$), of strictly less than 0.3%, preferably strictly less than 0.2%, relative to the total weight of the adsorbent, are preferred.

According to yet another preferred embodiment of the invention, the adsorbent comprises a content of potassium ions ($K^+$), expressed by weight of potassium oxide ($K_2O$), of less than 9%, preferably less than 8%, even better still less than 5%, and more preferably of between 0% and 2%, advantageously between 0% and 1%, limits included, relative to the total weight of the adsorbent.

Preferably, the total weight content of alkali or alkaline-earth metal ions other than $Ba^{2+}$, $K^+$ and $Sr^{2+}$, expressed by weight of alkali or alkaline-earth metal oxides respectively, is less than 5% and is preferably between 0% and 2% and advantageously between 0% and 1%, limits included, relative to the total weight of the adsorbent.

According to one embodiment of the present invention, the barium/strontium weight ratio in the adsorbent is greater than 15:1, typically between 15:1 and 400:1, preferably between 16:1 and 300:1, more preferably between 16:1 and 200:1.

The adsorbent of the present invention is preferably in the form of agglomerates, that is to say that it consists of crystals of zeolite(s) and/or at least one non-zeolite phase comprising at least one agglomeration binder allowing the cohesion of the crystals to one another.

The agglomeration binder may be zeolitizable. It then contains at least 80%, preferably at least 90%, more preferably at least 95%, more particularly at least 96%, by weight, of zeolitizable clay and may also contain other mineral binders such as bentonite, attapulgite, and the like. The term "zeolitizable clay" is intended to mean a clay or a mixture of clays which are capable of being converted into zeolite matter (i.e. active matter in the sense of the adsorption), usually by the action of an alkaline basic solution. The zeolitizable clay belongs in general to the family of kaolins, kaolinites, nacrites, dickites, hallyosite and/or metakaolins. Kaolin is preferred and is the most commonly used.

Other clays, such as in particular sepiolite or attapulgite, may also be used. In any event, the clays may be used in their crude form or may be subjected beforehand to one or more treatments, for example chosen from calcining, acid treatment, chemical modification, and the like.

Thus, the adsorbent according to the present invention comprises crystals of zeolite(s), and at least one non-zeolite phase (NZP), that is to say a non-crystalline phase which is essentially inert with respect to the adsorption. The degree of crystallinity of the adsorbent according to the invention is measured by X-ray diffraction analysis, known to those skilled in the art by the acronym XRD, as indicated below. It is, in general, greater than 80%, that is to say that the NZP is less than 20%.

In one preferred embodiment of the present invention, the weight content of non-zeolite phase (NZP) is less than 15%, preferably less than 10%, more preferably less than 5%. According to one entirely preferred aspect, the NZP of the adsorbent is between 0% and 15%, preferably between 0% and 10%, more preferably between 0% and 5%, limits not included, entirely preferably between 0.1% and 5%, even better still between 0.5% and 5% and most particularly preferably between 2% and 5%, limits not included, relative to the total weight of the anhydrous adsorbent (weight corrected with respect to loss on ignition).

The number-average diameter of the adsorbent according to the invention is advantageously and usually between 0.2 mm and 2 mm, more particularly between 0.2 mm and 0.8 mm and preferably between 0.2 mm and 0.65 mm, limits included.

According to one preferred embodiment, the adsorbent according to the invention has a loss on ignition, measured at 950° C. according to standard NF EN 196-2, of between 4.0% and 7.7%, preferably between 4.5% and 6.5% and advantageously between 4.8% and 6%, limits included.

The adsorbent according to the present invention preferentially has a mechanical strength generally greater than or equal to 1.8 MPa, typically greater than or equal to 2.1 MPa. This mechanical strength is measured by the Shell series SMS 1471-74 method adapted for agglomerates less than 1.6 mm in size.

The adsorption capacity of the adsorbent according to the invention is for its part measured by measuring the micropore volume of the adsorbent evaluated according to the Dubinin-Raduskevitch equation by adsorption of nitrogen ($N_2$) at a temperature of 77K, after degassing under vacuum at 300° C. for 16 hours. The micropore volume of the adsorbent of the invention is thus measured as being usually strictly greater than 0.245 $cm^3 \cdot g^{-1}$, preferably strictly greater than 0.250 $cm^3 \cdot g^{-1}$, more preferably between 0.250 $cm^3 \cdot g^{-1}$ and 0.300 $cm^3 \cdot g^{-1}$, limits not included.

The adsorbent according to the present invention, which advantageously comprises a reduced, or even very reduced, content of non-zeolite phase, that is to say phase essentially inert with respect to the adsorption, is an adsorbent that is entirely effective for separating xylenes and the production costs of which are reduced compared with adsorbents that are equivalent in terms of adsorption and known from the prior art.

The reduction of the production costs of these adsorbents is mainly obtained through the use of a barium salt of lower purity than that normally used for carrying out the cation exchange.

The adsorbent according to the invention may in fact be obtained according to any technique well known to those skilled in the art, and for example as described in patent application WO 2014/090771. The processes for synthesizing adsorbents, and in particular those intended for the separation of xylenes, generally comprises a step of agglomeration of crystals of zeolite(s) with a binder, usually a clay, a step of forming, then drying and calcining, and finally a step of cation exchange by bringing the agglomerate into contact with a solution of alkali and/or alkaline-earth metal ions.

In preferred embodiments, the agglomerate, before and/or after cation exchange, is subjected to one or more steps of zeolitization well known to those skilled in the art, as described for example in WO 2014/090771, that is to say conversion of all or at least part of the agglomeration binder into a zeolite crystal fraction, which is active in terms of adsorption.

In the case of xylene separation, the optimal cation exchange recognized in this technical field consists in exchanging all or at least most of the sodium ions present in the starting crystals of zeolite(s), with barium ions or barium ions and potassium ions. This ion exchange can be carried out, without distinction, on the crystals of zeolite(s) or on the agglomerates of crystals of zeolite(s) with the agglomeration binder, before and/or after optional zeolitization, preferably after zeolitization, of said binder.

The steps of exchange of the zeolite fraction cations is carried out according to the conventional methods known to those skilled in the art, and usually by bringing the crystals of zeolite(s), optionally agglomerated with a binder, before and/or after optional zeolitization, preferably after zeolitization, of said binder, into contact with a salt of the cation to be exchanged, such as barium chloride ($BaCl_2$) for exchange with barium, and/or potassium chloride (KCl) for exchange with potassium, in solution, usually in an aqueous solution, at a temperature of between ambient temperature and 100° C., and preferably of between 80° C. and 100° C.

In order to rapidly obtain low sodium oxide contents, as described above, the process is preferably carried out with a large excess of barium and/or potassium ions relative to the cations of the zeolite that it is desired to exchange, typically an excess of about from 10 to 12, advantageously by carrying out successive exchanges.

As indicated above, this cation exchange is usually carried out with an aqueous, organic or aqueous-organic solution, preferably an aqueous solution, comprising barium ions. The barium ion solutions used generally have a concentration of $Ba^{2+}$ ions that can range between 0.2 M and 2 M.

It has now been discovered, entirely surprisingly, that solutions of barium ions that may contain a degree of impurities, in the form of strontium salts, that can range up to 4% by weight make it possible to obtain adsorbents which have adsorption performances, in particular in the xylene separation application, that are entirely comparable to those of the adsorbent known from the prior art and for which cation exchanges are carried out with solutions of barium ions of much higher purity which are therefore more expensive.

More specifically, it has been observed that it is possible to use barium salts, in particular barium chloride, especially aqueous solutions of barium chloride, that may contain up to 4% by weight of impurities in strontium salt form, preferably between 0.2% and 3% by weight, preferably between 0.2% and 2.5% by weight, limits included, relative to the total weight of the barium salt in question.

The impurity in strontium salt form is usually strontium chloride ($SrCl_2$).

According to another aspect, the use of a barium salt comprising strontium in the proportions indicated above results in an adsorbent according to the invention for which the degree of strontium exchange is at most equal to 11%, preferably at most equal to 10%, more preferably at most equal to 9% and most particularly preferably between 0.5% and 8%. This degree of exchange corresponds to the molar ratio of the strontium oxide to the sum of the barium, strontium, potassium and sodium oxides.

Thus, the present invention proposes the use of barium salts of which the specification in terms of purity are reduced, while at the same time allowing the properties of the barium-exchanged adsorbent, in the application in question, to be maintained.

It is thus possible, by virtue of the present invention, to provide effective adsorbents that may contain strontium, the content of which, expressed as oxide (SrO) is strictly less than 3% by weight relative to the total weight of the adsorbent, thereby corresponding to a degree of strontium exchange of approximately at most 11% and to a content of impurities (strontium salt) at approximately 3% by weight in the barium solution used for the ion exchange.

These adsorbents can be used more particularly for the liquid-phase or gas-phase production of very pure para-xylene from a feedstock of aromatic hydrocarbons containing isomers comprising 8 carbon atoms.

Thus, and according to another aspect, the present invention provides a process for separating xylenes using an adsorbent as described above, allowing the production of high-purity para-xylene with optimized productivity, from a feedstock of aromatic hydrocarbons containing isomers comprising 8 carbon atoms.

More particularly, the invention relates to a process for recovering high-purity para-xylene from fractions of aromatic isomers comprising 8 carbon atoms, consisting in using an adsorbent according to the invention, used in liquid-phase processes but also in gas-phase processes as an adsorption agent for para-xylene in the presence of a desorbent, preferably chosen from toluene and para-diethylbenzene.

The term "high-purity para-xylene" is intended to mean a product suitable for use in the production of terephthalic acid or dimethyl terephthalate, that is to say a purity of at least 99.5% by weight, preferably at least 99.7% by weight, preferably at least 99.8% by weight and even more preferably at least 99.9% by weight. The purity of the para-xylene can be determined by chromatographic methods. A gas chromatography method that can be used for determining both the purity of the para-xylene and the specific amounts of impurities is the ASTM D-3798 method.

It is thus possible to separate the desired product (para-xylene) by (batchwise) preparative adsorption liquid chromatography, and advantageously continuously in a simulated moving bed, that is to say in simulated counter-current or simulated co-current mode, and more particularly in simulated counter-current mode.

The process for recovering para-xylene according to the invention using the adsorbent described according to the invention has the advantage of maximizing productivity, that is to say maximizing the flow of feedstock to be treated. This is particularly true under the following operating conditions for an industrial adsorption unit of simulated counter-current type:
number of beds: 6 to 30,
number of zones: at least 4 operating zones, each being located between a feed point and a drawing-off point,
temperature between 100° C. and 250° C., preferably between 150° C. and 190° C.,
pressure of the industrial unit between the xylene bubble-point pressure at the temperature of the process and 3 MPa,
ratio of desorbent/feedstock flow rates between 0.7 and 2.5, for example between 0.9 1.8, for a single ("stand alone") adsorption unit and between 0.7 and 1.4 for an adsorption unit combined with a crystallization unit,
recycling ratio (i.e. ratio of the average recycling flow rates (average flow rates of zones, weighted with respect to the number of beds per zone) to the feedstock flow rate) between 2.5 and 12, preferably between 3.5 and 6.

In this respect, reference may be made to the teaching of U.S. Pat. Nos. 2,985,589, 5,284,992 and 5,629,467. Operating conditions of an industrial simulated co-current adsorption unit are generally the same as those which operate in simulated counter-current mode, with the exception of the recycling ratio which is generally between 0.8 and 7. In this respect, reference may be made to the teaching of U.S. Pat. Nos. 4,402,832 and 4,498,991.

The desorption solvent may be any desorbent known to those skilled in the art and the boiling point of which is below that of the feedstock, such as toluene, but also a desorbent in which the boiling point is above that of the feedstock, such as para-diethylbenzene (PDEB). Selectivity of the adsorbents according to the invention for the adsorption of para-xylene contained in C8 aromatic fractions is optimal when the loss on ignition thereof, measured at 950° C., is generally between 4.0% and 7.7%, preferably between 4.5% and 6.5%, and very preferably between 4.8% and 6.0%, limits included.

In addition to the abovementioned use of separating xylene isomers, the present invention also relates to the uses of the adsorbents described above as adsorption agents capable of advantageously replacing the prior art adsorption agents for:
separating isomers of substituted toluene, such as nitrotoluene, diethyltoluene, toluenediamine, or the like,
separating cresols, and
separating polyhydric alcohols, such as sugars.

Finally, the invention relates to a process for recovering high-purity para-xylene from fractions of aromatic isomers comprising 8 carbon atoms, comprising the following successive steps:
a) a step of bringing the feedstock into contact with a bed of adsorbent comprising at least one zeolite adsorbent as defined according to any one of claims 1 to 8,
b) a step of bringing the bed of adsorbent into contact with a desorbent, preferably chosen from toluene and para-diethylbenzene in liquid phase or in gas phase.

Characterization Techniques

Crystal Particle Size:

The size of the number-average diameter of the zeolite X crystals used in step a) and of the crystals of zeolite X contained in the agglomerates is estimated by observation with a scanning electron microscope (SEM) or by observation with a transmission electron microscope (TEM).

In order to estimate the size of the zeolite crystals on the samples, a set of images is taken at a magnification of at least 5000. The diameter of at least 200 crystals is then measured using dedicated software, for example the Smile View software published by LoGraMi. The accuracy is of the order of 3%.

Chemical Analysis of the Zeolite Adsorbents—Si/Al Ratio, Oxide Weight Content and Degree of Exchange:

An elemental chemical analysis of the final product obtained at the end of the steps of the process of the invention described above can be carried out according to various analytical techniques known to those skilled in the art. Among these techniques, mention may be made of the technique of chemical analysis by x-ray fluorescence as described in standard NF EN ISO 12677: 2011 on a wavelength-dispersive spectrometer (WDXRF), for example the Tiger S8 machine from the company Bruker.

X-ray fluorescence is a non-destructive spectral technique which exploits the photoluminescence of atoms in the X-ray range, to establish the elemental composition of a sample. Excitation of the atoms, generally with an X-ray beam or by electron bombardment, generates specific radiations after return to the ground state of the atom. The X-ray fluorescence spectrum has the advantage of depending very little on the chemical combination of the element, which offers a precise determination, both quantitatively and qualitatively. A measurement uncertainty of less than 0.4% by weight is conventionally obtained after calibration for each oxide. In the present invention, the barium, strontium, silicon and aluminium contents are preferably measured by the X-ray fluorescence method described above.

On the other hand, for the elements that are lighter (relative to their atomic weight, such as the sodium or potassium present in the adsorbent), inductively coupled plasma-optical emission spectroscopy (ICP-OES) according to standard UOP 961-12 will be preferred in order to obtain greater accuracy.

ICP is a method of analysis by atomic emission spectroscopy, the source of which is a plasma generated by inductive coupling. This method is also commonly used to determine the contents of various elements, such as silicon, aluminium, potassium, sodium, barium and strontium. In the present invention, the sodium contents (and optionally potassium contents for low contents less than 0.5% by weight of oxide relative to the total mass of oxides) are preferably measured by the ICP method according to standard UOP 961-12. In this case, an uncertainty for sodium with regard to the measurement of less than 0.01% for the weight content of sodium oxide in the adsorbent and an uncertainty for potassium with regard to the measurement of less than 0.02% for the weight content of potassium oxide in the adsorbent are obtained.

These elemental chemical analyses make it possible both to verify the Si/Al atomic ratio of the zeolite within the agglomerate, and to verify the quality of the ion exchange performed in the process described above. In the description of the present invention, the measurement uncertainty for the Si/Al atomic ratio is 0.05.

The quality of the ion exchange is linked to the number of moles of sodium oxide ($Na_2O$) remaining in the agglomerated zeolite adsorbent after exchange. More specifically, the degree of exchange with barium ions is estimated by evaluating the ratio between the number of moles of barium oxide, BaO, and the number of moles of the combination ($BaO+K_2O+SrO+Na_2O$). Likewise, the degree of exchange with strontium ions is estimated by evaluating the ratio between the number of moles of strontium oxide (SrO) and the number of moles of the combination ($BaO+SrO+Na_2O+K_2O$). It should be noted that the contents of various oxides are given as percentage by weight relative to the total weight of the anhydrous adsorbent (weight corrected with respect to loss on ignition).

Zeolite Adsorbent Particle Size:

The number-average diameter of the zeolite adsorbents obtained at the end of the agglomeration and forming step is determined by analysis of the particle size distribution of a sample of agglomeratate by imaging according to standard ISO 13322-2:2006, using a conveyor belt which allows the sample to pass in front of the camera lens.

The number-average diameter is then calculated from the particle size distribution by applying standard ISO 9276-2:2001. In the present document, the term "number-average diameter" or else "size" is used for the adsorbents according to the invention, with a precision of about 0.01 mm.

Zeolite Adsorbent Mechanical Strength:

The technique for characterizing the mechanical strength representative of the crushing of the adsorbent in a bed or a reactor is the bulk mechanical strength characterization technique, as described in the Shell Method Series SMS 1471-74 (Shell Method Series SMS1471-74 Determination of Bulk Crushing Strength of Catalysts. Compression-Sieve Method"), associated with the "BCS Tester" machine sold by the company Vinci Technologies. This method, initially intended for the characterization of catalysts of 3 to 6 mm, is based on the use of a 425 µm sieve which will make it possible in particular to separate the fines created during the crushing.

The use of a 425 µm sieve remains suitable for particles with a diameter greater than 1.6 mm, but must be adapted according to the particle size of the adsorbents that it is desired to characterize. Standard ASTM D7084-04, which also describes a method for measuring the bulk crush strength of catalysts ("Determination of Bulk Crush Strength of Catalysts and Catalyst Carriers"), defines the passing through of the sieve to be used as being equal to half the diameter of the particles of catalysts to be characterized.

The method provides for a preliminary step of sieving the sample of catalysts or adsorbents to be characterized. If an amount equal to 10% by weight of the sample passes through the screen, a sieve with a smaller through-size will be used.

The adsorbents of the present invention, generally in the form of balls or extrudates, in general have a number-average diameter or a length, i.e. largest dimension in the case of non-spherical agglomerates, of between 0.4 mm and 2 mm and in particular of between 0.4 mm and 0.8 mm and preferably between 0.4 mm and 0.65 mm. Consequently, a sieve that is adapted such that less than 10% by weight of the sample passes through the screen during a prior sieving step is used in place of the 425 µm sieve mentioned in the Shell SMS1471-74 standard method.

The measurement protocol is the following: a 20 cm³ sample of agglomerates pre-sieved with the appropriate sieve (200 µm) and pre-dried in an oven for at least 2 hours at 250° C. (instead of 300° C. mentioned in the Shell SMS1471-74 standard method), is placed in a metal cylinder with a known internal cross section. An increasing force is applied stepwise to this sample by means of a piston, through a bed of 5 cm³ of stainless steel balls in order to give a better distribution of the force exerted by the piston on the adsorbents (use of balls 2 mm in diameter for spherically shaped particles with a diameter strictly less than 1.6 mm). The fines obtained at the various pressure steps are separated by sieving (appropriate sieve of 200 µm) and weighed.

The bulk crush strength is determined by the pressure in megapascals (MPa) for which the amount of accumulated fines passing through the sieve comes to 0.5% by weight of the sample. This value is obtained by plotting, on a graph, the mass of fines obtained as a function of the force applied to the bed of adsorbent and by interpolating with respect to 0.5% by mass of the accumulated fines. The mechanical bulk crush strength is typically between a few hundred kPa and a few tens of MPa and is generally between 0.3 MPa and 4 MPa. The precision is conventionally less than 0.1 MPa.

Non-Zeolite Phase of the Zeolite Adsorbents:

The amount of non-zeolite phase, for example non-zeolitized residual binder or any other amorphous phase, after zeolitization is calculated according to the following equation:

$$NZP=100-\Sigma(ZP),$$

where ZP represents the sum of the amounts of the zeolite X fractions within the meaning of the invention.

The amount of the zeolite X fractions is measured by a x-ray diffraction analysis, known to those skilled in the art by the acronym XRD. This analysis is performed on a Bruker brand machine, and the amount of the zeolite X fractions is then evaluated using the TOPAS software from the company Bruker. This method also makes it possible to determine the nature of the various zeolite fractions present in the adsorbent of the present invention.

Micropore Volume:

The crystallinity of the agglomerates is also evaluated by measuring their micropore volume while comparing it to that of a suitable reference (zeolite that is 100% crystalline under identical cationic treatment conditions or theoretical zeolite). This micropore volume is determined from the measurement of the adsorption isotherm of gas, nitrogen, at its liquefaction temperature. Prior to the adsorption, the zeolite-based adsorbent is degassed at between 300° C.-450° C. for a time of from 9 hours to 16 hours, under vacuum ($P<6.7\times10^{-4}$ Pa). Measurement of the nitrogen adsorption isotherm at 77K is then performed on a machine of ASAP 2010 M type from Micromeritics, taking at least 35 measurement points at relative pressures of ratio $P/P_0$ between 0.002 and 1. The micropore volume is determined according to Dubinin and Raduskevitch from the isotherm obtained, by applying standard ISO 15901-3 (2007). The micropore volume evaluated according to Dubinin and Raduskevitch is expressed in $cm^3$ of liquid adsorbate per gram of anhydrous adsorbent. The measurement uncertainty is $\pm0.003$ $cm^3$ $g^{-1}$.

Loss on Ignition of the Zeolite Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Characterization of the Adsorption in Liquid Phase by Breakthrough:

The technique used to characterize the adsorption of molecules in liquid phase on a porous solid is the "breakthrough" technique, described by Ruthven in "Principles of Adsorption and Adsorption Processes" Chapters 8 and 9, John Wiley & Sons (1984), which defines the breakthrough curves technique as the study of the response to the injection of a scale of adsorbable constituents. The analysis of the mean exit time (first moment) of the breakthrough curves provides information on the amounts adsorbed and also makes it possible to evaluate the selectivities, that is to say the separation factor, between two adsorbable constituents. The injection of a non-adsorbable constituent used as tracer is recommended for estimating the non-selective volumes. The analysis of the dispersion (second moment) of the breakthrough curves makes it possible to evaluate the equivalent height of theoretical plates, based on the representation of a column by a finite number of hypothetical reactors that are ideally stirred (theoretical stages), which is a direct measurement of the axial dispersion and of the resistance to material transfer of the system.

EXAMPLES

The examples which follow illustrate the invention without, however, limiting it in any way whatsoever, and the scope of protection of which is specified by the appended claims.

General Method for Preparing an Adsorbent According to the Invention Based on Zeolite X with an Si/Al Molar Ratio=1.25

A homogeneous mixture is prepared and 800 g of zeolite NaX crystals are agglomerated according to the procedure described in patent application WO 2014/090771 (synthesis of example B) with 105 g of kaolin (expressed in calcined equivalent) and 45 g of colloidal silica sold under the trade name Klebosol®30 (containing 30% by weight of $SiO_2$ and 0.5% of $Na_2O$) with the amount of water which allows extrusion of the mixture.

The extrudates are dried, crushed in such a way as to recover the grains of which the number-average diameter is equal to 0.5 mm, then calcined at 550° C. under a nitrogen stream for 2 hours.

The agglomerate obtained (200 g) is placed in a glass reactor equipped with a jacket regulated at a temperature of 100° C.±1° C. 1.5 l of an aqueous sodium hydroxide solution having a concentration of 2.5 M are then added and the reaction medium is left to stir for a period of 4 hours.

The agglomerates are then washed in water in 3 successive washing operations, followed by emptying of the reactor. The washing is known to have been efficient when the final pH of the washing waters measured is between 10.0 and 10.5.

The sodium cations of the agglomerates obtained are exchanged at 95° C. with barium and strontium ions. For this, various amounts of strontium salt, of formula $SrCl_2.6H_2O$, are added to the barium salt, of formula $BaCl_2.2H_2O$, (pure, containing at most 0.2% by weight of strontium chloride), such that the mass percentage of $SrCl_2$ salt is equal to the percentage indicated in Table 1 below.

For example, an exchange solution is prepared by dissolving 150 g of $BaCl_2.2H_2O$ salt with 1.4 g of $SrCl_2.6H_2O$ salt in 1 l of water. The amount of strontium salt corresponds to 0.9% by weight relative to the total mass of salt. Next, 10 g of agglomerates prepared above are brought into contact with this solution in order to carry out the cation exchange.

The exchange is carried out in 4 steps. At each step, the volume of solution to mass of solid ratio is 25 ml·$g^{-1}$ and the exchange is continued for 4 hours each time. Between each exchange, the solid is washed several times so as to remove the excess salt therefrom. The agglomerates are then dried at 80° C. for 2 hours and, finally, activated at 250° C. for 2 hours under a nitrogen stream The loss on ignition measured, as described above, is 5.5%±0.1% for each sample. The degree of barium+strontium exchange of the adsorbents is calculated from the elemental analyses by X-ray fluorescence of the barium, strontium and sodium oxides as described in the characterization techniques.

In the example given above, the degree of barium exchange is 95.1%, and the degree of strontium exchange is 4.0%.

The other examples are carried out starting from 150 g of barium salt, to which is added the amount of $SrCl_2$ salt which makes it possible to obtain the weight % values that are indicated for the examples according to the invention and the comparative examples.

Reference Example A

This example corresponds to Example 1 of application WO 2014/090771 and corresponds to an adsorbent exchanged with barium alone, with a very low sodium content (cf. Table 1).

The degree of barium exchange calculated according to the X-ray fluorescence analysis of this agglomerate is 99.1% and the loss on ignition is 5.4%.

Reference Example B

This second reference example is carried out in a manner identical to Example 1 of application WO 2014/090771, but is stopped at the second exchange. The agglomerates are involved in a reaction of cation exchange through the action of a 0.5 M aqueous barium chloride solution at 95° C. in only 2 steps. At each step, the volume of solution to mass of solid ratio is 20 ml·g$^{-1}$ and the exchange is continued for 4 hours each time. Between each exchange, the solid is washed several times so as to remove the excess salt therefrom. The agglomerates are then dried at 80° C. for 2 hours and, finally, activated at 250° C. for 2 hours under a nitrogen stream.

The degree of barium exchange of this agglomerate is 92.6% and the loss on ignition is 5.5%.

Examples 1 to 5 and the comparative example are carried out according to reference example A using solutions of barium chloride containing increasing contents of strontium chloride, in order to simulate solutions of barium chloride containing strontium as impurity.

The details of each of Examples 1 to 5 and of the Comparative Example are reproduced in Table 1 below:

TABLE 1

| Example | % SrCl$_2$ | % BaO | % SrO | % Na$_2$O | Ba/Sr |
|---|---|---|---|---|---|
| Example A | 0 | 37.6 | 0 | <0.1 | 0 |
| Example B | 0 | 34.3 | 0 | 1.1 | 0 |
| Example 1 | 0.4 | 35.8 | 0.5 | <0.2 | 75.8 |
| Example 2 | 0.9 | 34.9 | 1.0 | <0.2 | 35.0 |
| Example 3 | 1.7 | 34.8 | 1.7 | <0.2 | 21.1 |
| Example 4 | 2.0 | 34.8 | 2.0 | <0.2 | 18.4 |
| Example 5 | 2.5 | 34.2 | 2.4 | <0.2 | 15.1 |
| Comparative Example | 4.8 | 33.8 | 3.7 | <0.2 | 9.7 |

In Table 1 above:
- % SrCl$_2$ denotes the weight percentage of strontium chloride hexahydrate in the barium chloride solution (comprising barium and impurities) used to carry out the cation exchange;
- % BaO denotes the weight percentage of barium oxide relative to the total weight of the anhydrous adsorbent;
- % SrO denotes the weight percentage of strontium oxide relative to the total weight of the anhydrous adsorbent;
- % Na$_2$O denotes the weight percentage of sodium oxide relative to the total weight of the anhydrous adsorbent;
- Ba/Sr denotes the barium/strontium weight ratio in the anhydrous adsorbent.

Breakthrough Test

A breakthrough test (frontal chromatography) is then carried out on the agglomerates obtained in Example 1 in order to evaluate their efficiency. The amount of adsorbent used for this test is approximately 30 g.

The procedure for obtaining the breakthrough curves is the following:
- Filling the column with the sieve and placing in the test bench.
- Filling with a solvent (toluene) at ambient temperature.
- Gradual increase to the adsorption temperature under a stream of solvent (2 cm$^3$·min$^{-1}$).
- Injection of solvent at 2 cm$^3$·min$^{-1}$ when the adsorption temperature is reached.
- Solvent/feedstock permutation to inject the feedstock (2 cm$^3$·min$^{-1}$).
- Injection of the feedstock is then maintained for a time sufficient to reach thermodynamic equilibrium.
- Collection of the breakthrough product in a single flask then analysis of the composition of the product by GC.

The pressure is sufficient for the feedstock to remain in the liquid phase, i.e. 1 Ma. The adsorption temperature is 175° C. The composition of the feedstock used for the tests is the following:
- Para-xylene: 18% by weight
- Meta-xylene: 18% by weight
- Ortho-xylene: 18% by weight
- Ethylbenzene: 18% by weight
- Para-diethylbenzene: 18% by weight
- Isooctane: 10% by weight (this is used as a tracer for estimating the non-selective volumes and is not involved in the separation).

The binary selectivities of the compounds in pairs, denoted binary selectivities $\alpha_{i/k}$, are calculated from the adsorbed amounts $q_i$ and $q_k$ of the compounds i and k, the latter being determined by the material balance from the analysis of the composition of the breakthrough product and of the composition of the feedstock (in which feedstock the mass fraction of the compounds i and k is $y_i$ and $y_k$):

$$\alpha_{i/k} = \frac{q_i y_k}{q_k y_i}$$

The evaluation of the potential of these adsorbents during the simulated counter-current implementation is carried out on the basis of the equilibrium theory applied to multicomponent systems with constant selectivities, as described by Mazotti, Storti and Morbidelli in "*Robust Design of Countercurrent Adsorption Separation Processes: 2. Multicomponent Systems*", AIChE Journal, (November 1994), Vol. 40, No. 11.

In particular, reference is made in this case to equation 8, which describes the conditions to be met with regard to the reduced flow rates $m_j$ of the 4 sections (j=1 to j=4) of a counter-current separation unit as represented diagrammatically in figure 1 of the article cited, in order to obtain complete separation.

$$\text{Section 1: } K_{ss} < m_1 \delta_1 < +\infty \tag{8}$$

$$\text{Section 2: } K_{wk} < m_2 \delta_2 < K_{sk}$$

$$\text{Section 3: } K_{wk} < m_3 \delta_3 < K_{sk}$$

$$\text{Section 4: } -\frac{\epsilon_p \delta_4}{\sigma(1-\epsilon_p)} < m_4 \delta_4 < K_{ww}.$$

This equation 8 refers to the adsorptivities $K_i$ of the various constituents, and also to the parameter $\delta_j$ of each section j defined by equation 7:

$$\delta_j = \sum_{l=1}^{NC} K_l y_l \quad (j = 1, \ldots, 4), \tag{7}$$

It should be noted here that, by definition, the binary selectivity $\alpha_{i/k}$ between the compounds i and k is equal to the ratio of the adsorptivities $K_i/K_k$.

The reduced flow rate "m" of each section of the unit is defined as being the ratio of the flow rate of the liquid phase to the flow rate of the adsorbed phase. Equation 8 indicates which are the limiting reduced flow rates for each section. In a 4-section counter-current separation unit, the feedstock flow rate corresponds to the difference between the reduced flow rate in zone 3 and the reduced flow rate in zone 2.

Consequently, when it is desired to evaluate the maximum productivity that can be achieved with a given adsorbent, it is sought to evaluate the maximum amount of feedstock that it will be possible to treat, that is to say to evaluate the difference between the maximum reduced flow rate in zone 3 and the minimum reduced flow rate in zone 2.

It will be possible to compare the performances in terms of maximum productivity of two adsorbents by comparing their maximum reduced flow rate of feedstock determined from the reduced flow rates of zones 2 and 3, respectively $m_2$ and $m_3$, according to the relationship:

$$\max(m_{Feedstock}) = \max(m_3) - \min(m_2).$$

If a constant-selectivity system is considered, the composition of the liquid phase which gives the highest stress in zone 2 and in zone 3 is the composition of the liquid phase at the point of injection of the feedstock into the unit. Indeed, starting from this point, the concentration of para-xylene, which is the compound most adsorbed, increases in the direction of circulation of the solid in zone 2 and decreases in the direction of circulation of the liquid in zone 3. The composition at this point can be approximated to the composition of the feedstock to be treated, and it is this composition that will be used to evaluate the terms $\delta_2$ and $\delta_3$ of equation 8. The terms $\delta_2$ and $\delta_3$ being defined by equation 7 mentioned above.

For each adsorbent, this max reduced flow rate ($m_{Feedstock}$) is calculated from the values of binary selectivities measured experimentally. Table 2 makes it possible to compare the maximum reduced flow rate of feedstock "$\max(m_{Feedstock})$" for each of the adsorbents tested. The maximum reduced flow rate of feedstock "$\max(m_{Feedstock})$" is representative of the productivity; the higher its value, the better the productivity.

TABLE 2

| | $\alpha_{PX/MX}$ | $\alpha_{PX/EB}$ | $\max(m_{Feedstock})$ |
|---|---|---|---|
| Example A | 3.10 | 2.30 | 1.17 |
| Example B | 2.92 | 2.23 | 1.11 |
| Example 2 | 3.26 | 2.26 | 1.18 |
| Comparative example | 2.85 | 2.19 | 1.08 |

It is noted that the $\max(m_{Feedstock})$ reduced flow rate remains substantially the same whether it is an adsorbent of which the ion exchange has been carried out with a solution of barium chloride that is "pure" (i.e. free of strontium impurity) (Example A) or an adsorbent prepared from a solution of barium chloride that also contains strontium chloride (Example 2).

On the other hand, when the barium chloride contains sodium at contents comparable to strontium (owing to the partial exchange with barium), it is noted that the max ($m_{Feedstock}$) productivity is reduced. This observation effectively confirms, in addition to the effect on selectivity, the advantage of barium exchange for separating xylenes, which is perfectly known to those skilled in the art.

Likewise, it has been observed that, when the content of strontium impurities in the barium chloride solution is too high, in particular greater than 4% (cf. Comparative example, strontium chloride content >4.8%), the $\max(m_{Feedstock})$ productivity drops drastically.

These examples confirm in all respects the subject of the present invention and make it possible to demonstrate that it is entirely possible to envisage the presence of strontium ions in barium-exchange adsorbents that can be used for separating xylenes, without however affecting the para-xylene productivity. Moreover, an improvement in selectivity for para-xylene is obtained.

The invention claimed is:

1. An adsorbent comprising an agglomeration of zeolite crystals, the adsorbent comprising:
   crystals of FAU zeolite(s), with an Si/Al molar ratio of between 1.00 and 1.50, limits included;
   a weight content of barium ions ($Ba^{2+}$), expressed by weight of barium oxide (BaO), greater than 30%, relative to the total weight of the adsorbent; and
   a weight content of strontium ions ($Sr^{2+}$), expressed by weight of strontium oxide (SrO), greater than 0.1% and less than 3%, relative to the total weight of the adsorbent.

2. The adsorbent according to claim 1, having an Si/Al atomic ratio of between 1.00 and 2.00, limits included.

3. The adsorbent according to claim 1, wherein the total weight content of alkali or alkaline-earth metal ions other than $Ba^{2+}$ and $Sr^{2+}$, expressed by weight of alkali or alkaline-earth metal oxides, is less than 5%, relative to the total weight of the adsorbent.

4. The adsorbent according to claim 1, wherein the weight content of sodium ions ($Na^+$), expressed by weight of sodium oxide ($Na_2O$), is less than 0.3%, relative to the total weight of the adsorbent.

5. The adsorbent according to claim 1, wherein the weight content of potassium ions ($K^+$), expressed by weight of potassium oxide ($K_2O$), is less than 9%, relative to the total weight of the adsorbent.

6. The adsorbent according to claim 1, having a barium/strontium weight ratio of greater than 15:1.

7. The adsorbent according to claim 1, having a weight content of a non-zeolite phase (NZP) of less than 15%, relative to the total weight of the adsorbent, when the adsorbent is anhydrous.

8. A process for liquid-phase or gas-based production of purified para-xylene from a feedstock of aromatic hydrocarbons containing isomers comprising 8 carbon atoms that include para-xylene, the process comprising contacting the feedstock with the adsorbent according to claim 1.

9. A process for recovering purified para-xylene from a feedstock comprising fractions of aromatic isomers comprising 8 carbon atoms that include para-xylene, the process comprising the following successive steps:
   a) bringing the feedstock into contact with the adsorbent according to claim 1,
   b) bringing the adsorbent into contact with a desorbent in liquid phase or in gas phase.

* * * * *